US011089986B2

(12) United States Patent
Eger et al.

(10) Patent No.: US 11,089,986 B2
(45) Date of Patent: Aug. 17, 2021

(54) MEASUREMENT SIGNAL AMPLIFIER AND A METHOD FOR SUPPLYING ENERGY TO A MEASUREMENT SIGNAL AMPLIFIER

(71) Applicant: Drägerwerk AG & Co. KGaA, Lübeck (DE)

(72) Inventors: Marcus Eger, Lübeck (DE); Frank Sattler, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 724 days.

(21) Appl. No.: 15/561,736

(22) PCT Filed: Mar. 24, 2016

(86) PCT No.: PCT/EP2016/000511

§ 371 (c)(1),
(2) Date: Sep. 26, 2017

(87) PCT Pub. No.: WO2016/155876

PCT Pub. Date: Oct. 6, 2016

(65) Prior Publication Data

US 2018/0085017 A1 Mar. 29, 2018

(30) Foreign Application Priority Data

Mar. 31, 2015 (DE) .................... 10 2015 004 113.4

(51) Int. Cl.
*A61B 5/30* (2021.01)
*A61B 5/00* (2006.01)
(Continued)

(52) U.S. Cl.
CPC ................ *A61B 5/30* (2021.01); *A61B 5/349* (2021.01); *A61B 5/389* (2021.01); *A61B 5/7225* (2013.01); *A61B 2560/0214* (2013.01)

(58) Field of Classification Search
CPC .......................... A61B 5/04004; A61B 5/0452
(Continued)

(56) References Cited

U.S. PATENT DOCUMENTS 4,248,240 A * 2/1981 van Eykern ....... A61B 5/04004 600/484
2006/0122529 A1 6/2006 Tsau
(Continued)

FOREIGN PATENT DOCUMENTS

DE 29 10 944 A1 10/1979
EP 23 71 412 A1 10/2011
(Continued)

*Primary Examiner* — Nadia A Mahmood
(74) *Attorney, Agent, or Firm* — McGlew and Tuttle, P.C.

(57) ABSTRACT

A measured signal amplifier (1) amplifies an EMG sensor signal (E). The measured signal amplifier (1) includes a sensor interface (2) for receiving the EMG sensor signal (E), at least one device interface (3) for receiving an electrical energy signal as well as for transmitting a processed signal (V), an electrically chargeable energy storage device (4) and at least one computer (5). The computer (5) is configured to derive a processed signal (V) from the EMG sensor signal (E) and to control the charging of the energy storage device (4) by the electrical energy signal as a function of the EMG sensor signal (E) received from the sensor interface (2).

17 Claims, 2 Drawing Sheets

1 2 5 3
4

(51) Int. Cl.
*A61B 5/349* (2021.01)
*A61B 5/389* (2021.01)

(58) Field of Classification Search
USPC .......................................................... 600/516
See application file for complete search history.

(56) References Cited

U.S. PATENT DOCUMENTS

| | | | | |
|---|---|---|---|---|
| 2007/0032733 | A1* | 2/2007 | Burton | A61B 5/4812 600/509 |
| 2007/0129769 | A1 | 6/2007 | Bourget et al. | |
| 2011/0240021 | A1 | 10/2011 | Eger et al. | |

FOREIGN PATENT DOCUMENTS

| | | | |
|---|---|---|---|
| JP | 2001-148962 | A | 6/2001 |
| JP | 2007-517553 | A | 7/2007 |
| WO | 2005/096924 | A1 | 10/2005 |

* cited by examiner

MEASUREMENT SIGNAL AMPLIFIER AND A METHOD FOR SUPPLYING ENERGY TO A MEASUREMENT SIGNAL AMPLIFIER

CROSS REFERENCE TO RELATED APPLICATIONS

This application is a United States National Phase Application of International Application PCT/EP2016/000511, filed Mar. 24, 2016, and claims the benefit of priority under 35 U.S.C. § 119 of German Application 10 2015 004 113.4, filed Mar. 31, 2015, the entire contents of which are incorporated herein by reference.

FIELD OF THE INVENTION

The present invention pertains to a measured signal amplifier for amplifying an EMG sensor signal, to a medical system having a measured signal amplifier according to the present invention, as well as to a method for operating a measured signal amplifier.

BACKGROUND OF THE INVENTION

Electrical activities of muscles are measured in medical electrodiagnostics, e.g., within the framework of an electromyography (EMG), in order to obtain information on the health status of nerve as well as muscle cells from this. Relationships between the force of a muscle and frequencies or amplitudes of electrical signals measured during the activity of the muscle are determined in the area of biomechanics in sports medicine in order to improve, for example, movements of athletes based on this.

The membrane potential of a muscle cell, which potential is to be measured, equals about 70 mV less in the interior of the muscle cell than outside it. There is a local reversal of the membrane potential during muscle activity, which lasts about 1 msec and can be determined by measurement. Measured signal amplifiers, e.g., biopotential amplifiers are used to generate displayable signals from these measurement results. Measured signal amplifiers, which amplify an electrical potential, are also called electrical differential amplifiers.

Common-mode rejection, which is also called "Common-Mode Rejection Ratio" (CMRR), is a problem in connection with the amplification of measured signals. Common-mode rejection designates a change in the output voltage of such a measured signal amplifier during a simultaneous change in the two input voltages by the same amount. The output voltage remains constant in this case in an ideal measured signal amplifier, because this output voltage depends exclusively on the difference of the two input voltages. A real measured signal amplifier has a change in the output voltage in this case. The poorer the common-mode rejection, the greater is the change in the output voltage of the measured signal amplifier.

To improve the rejection, high-quality measured signal amplifiers have an electrical energy storage device, which is configured, e.g., as a rechargeable battery or capacitor. Charging of the energy storage device brings about a marked worsening of the common-mode rejection for the duration of the charging, so that the measured signal amplifier provides measurement results with greater measuring inaccuracies during this time period.

US 2011/0240021 A1 discloses a measured signal amplifier for amplifying biosignals, which has a plurality of modules with an energy storage device each to improve the common-mode rejection, wherein said energy storage devices are alternatingly rechargeable decoupled from one another. One module with charged energy storage device can consequently be used to amplify the measured signal, while the energy storage device of another module is being charged. In this manner, there is no galvanic connection between the measured signal amplifier and a therapy device, e.g., a monitor, a ventilator or anesthesia device, even during the charging of a decoupled energy storage device. Such a measured signal amplifier has the drawback that a plurality of modules are necessary for amplifying the measured signals. This leads to increased space requirement, to an increase in the manufacturing costs as well as to an increase in parasitic capacitance.

In alternative solutions, the measured signal amplifier has, instead of an energy storage device, a supply line for supplying the measured signal amplifier with electric current. Such measured signal amplifiers require the use of a d.c.-d.c. converter, which is arranged close to the measured signal amplifier and which converts a d.c. voltage of a first value into a d.c. voltage of a second value. Such d.c.-d.c. converters usually have a relatively poor efficiency, which equals about 35% and thus leads, in addition to an increased energy consumption, to increased generation of heat. This heat may lead to discomfort and to damage to the patient's skin, especially in case of measured signal amplifiers arranged directly at the patient.

SUMMARY OF THE INVENTION

Based on this state of the art, a basic object of the present invention is to provide a medical system with a measured signal amplifier as well as a method for operating a measured signal amplifier, which are at least partially free from these drawbacks. Therefore, an object of the present invention is to provide a measured signal amplifier that can be manufactured in a relatively cost-effective manner, has a compact design, improved common-mode rejection and at the same time amplifies measured signals in a reliable manner. Furthermore, an object of the present invention is to provide a method for operating a measured signal amplifier, which guarantees sufficient energy supply for the measured signal amplifier along with reliable amplification of measured signals.

Accordingly, the object is accomplished by a measured signal amplifier for amplifying an EMG sensor signal, having a sensor interface for receiving the EMG sensor signal, at least one device interface for receiving an electrical energy signal as well as for transmitting a processed signal, an electrically chargeable energy storage device, as well as at least one computer. The computer is configured to derive a processed signal from the EMG sensor signal as well as to control the charging of the energy storage device by means of the electrical energy signal as a function of the EMG sensor signal received from the sensor interface.

An EMG sensor signal is a measured variable of electromyography and is generated by measuring the electrical muscle activity of a patient. In case of rhythmic or periodic muscle activity, e.g., in case of the heart muscle, the EMG sensor signal has at least essentially a periodicity, i.e., recurring characteristics. This makes it possible to divide the EMG sensor signal into diagnostically relevant and diagnostically irrelevant segments. By hiding the diagnostically irrelevant segments, a diagnostic result of electromyography is thus not essentially compromised negatively.

The sensor interface is configured to receive the EMG sensor signal and has for this, for example, a corresponding connection jack for an EMG sensor.

The device interface is configured to receive an electrical energy signal, e.g., an energy signal of an energy source. A power supply of the measured signal amplifier is thus guaranteed via the device interface. The device interface is preferably configured to intermittently receive energy signals. Moreover, the device interface is configured to transmit a processed signal, which is derived from the EMG sensor signal, for example, to a therapy device and/or to a display unit.

The energy storage device is preferably configured in a size-optimized manner. The energy storage device therefore preferably has a capacitance that is as high as necessary and as small as possible, in order to thus make possible the smallest possible overall size of the measured signal amplifier.

The computer is configured to derive the processed signal from the EMG sensor signal. The processed signal is preferably a measurement-based amplification of the EMG sensor signal for increasing the usability or evaluability thereof. The computer is configured to receive and generate electrical signals. The computer is further configured to control the charging of the energy storage device on the basis of the received EMG sensor signal. This is preferably carried out by an analysis of the received EMG sensor signal and by a differentiation between relevant areas of the EMG sensor signal and irrelevant areas of the EMG sensor signal. The computer is preferably configured to identify irrelevant areas of the EMG sensor signal and to make possible the charging of the energy storage device at the time of reception of such irrelevant areas of the EMG sensor signal.

A basic idea of the present invention is that charging of an energy storage device of a measured signal amplifier can take place at times at which negative effects occurring during such a charging are negligible, because these have only a relatively minor effect on the quality of an output signal of the measured signal amplifier or output signals of the measured signal amplifier are not necessary at these times. This has the advantage that the measured signal amplifier requires a relatively small installation space due to the relatively small energy storage device and thus it can be manufactured in a cost-effective manner and can be used in a flexible manner. Furthermore, it is guaranteed by the measured signal amplifier according to the present invention that all measurement results that are of interest for a user, i.e., the relevant areas of the EMG sensor signal, can be displayed with improved accuracy than in case of comparable wired applications.

Furthermore, provisions are made for the computer to be configured to prevent the output of the processed signal during the charging of the energy storage device. Since charging of the energy storage device preferably takes place only or essentially during the reception of areas of the EMG sensor signal that are irrelevant for a diagnosis, the suppression of such irrelevant EMG sensor signals has the advantage that markedly fewer erroneous EMG sensor signals are transmitted. Further, charging of the energy storage device may bring about a distortion of EMG sensor signals, so that such signals are unusable for a further analysis anyway.

Provisions may preferably be made for the energy storage device to have a capacitor. Such an energy storage device can be charged rapidly and is configured for storing sufficient charge to guarantee reliable measured signal amplification of relevant EMG sensor signals until the next charging. Moreover, the capacitor preferably has a weight- and space-saving configuration.

Further, the capacitor is preferably configured as a Gold Cap capacitor. Such a capacitor can be charged especially rapidly and is configured for storing sufficient charge to guarantee reliable measured signal amplification of relevant EMG sensor signals until the next charging. Further, a Gold Cap capacitor has an especially weight- and space-saving configuration.

Provisions may preferably be made for the computer to be further configured to determine, based on the received EMG sensor signal, a first time period in which the EMG sensor signal has a heart signal component of a QRS complex as well as to control the charging of the energy storage device such that the energy storage device is charged during the first time period. A QRS complex is an area of the EMG sensor signal that is irrelevant for a diagnosis and can easily be identified by the computer by an analysis of the EMG sensor signal based on certain characteristics. The influence of the received EMG sensor signal by charging of the energy storage device is therefore irrelevant at the time of a QRS complex. This has the advantage that relevant EMG sensor signals that do not have a QRS complex are not distorted by any charging. Higher quality of the processed signal is thus guaranteed.

Further, provisions may preferably be made for the computer to be configured to suppress the output of the processed signal during the first time period. The computer is thus configured not to output any processed signal during the reception of a QRS complex or during the charging. This has the advantage that no irrelevant processed signals, especially processed signals based of EMG sensor signals distorted by the charging, are consequently outputted.

Provisions may be made in an especially preferred embodiment of the measured signal amplifier according to the present invention for the computer to be configured to determine, on the basis of the EMG sensor signal received, a second time period, in which the EMG sensor signal has no heart signal component of a QRS complex and to control the charging of the energy storage device such that the energy storage device is not charged during the second time period. An EMG sensor signal that has no heart signal component of a QRS complex is at least essentially a relevant EMG sensor signal. It is thus advantageously ensured that the relevant EMG sensor signal is not distorted by a charging of the energy storage device. The reliability and the accuracy of the measured signal amplifier are thus advantageously improved.

According to a second aspect of the present invention, the object is accomplished by a medical system, having at least one therapy device and at least one EMG sensor for generating an EMG signal as well as a measured signal amplifier according to the present invention. The medical system has the advantage that the measured signal amplifier requires a relatively small space for installation based on the small energy storage device and thus the medical system can be manufactured in a cost-effective manner and can be used in a flexible manner. Furthermore, it is guaranteed by the medical system according to the present invention that all the measurement results that are of interest for a user, i.e., the relevant areas of the EMG sensor signal, can be displayed with improved accuracy compared to comparable wired applications.

The medical system preferably has a power supply unit, which is configured for intermittent supply of the energy storage device of the measured signal amplifier with electrical energy. The power supply unit can preferably be controlled by the computer. This has the advantage that optimal charging of the energy storage device is ensured with simple means, without relevant EMG sensor signals being adversely affected.

Furthermore, the object is accomplished according to the present invention by a method for operating a measured signal amplifier for amplifying an EMG sensor signal, having the steps of

- receiving an EMG sensor signal,
- determining a first time period, in which the EMG sensor signal has a heart signal component of a QRS complex,
- charging of an energy storage device of the measured signal amplifier with electrical energy within the first time period,
- determining a second time period, in which the EMG sensor signal has no heart signal component of a QRS complex, and
- preventing the charging of the energy storage device during the second time period.

The method has the advantage that all the measurement results that are of interest for a user, i.e., the relevant areas of the EMG sensor signal, can be displayed with improved accuracy than in comparable wired applications. Further, charging of the energy storage device only takes place at times at which an irrelevant EMG sensor signal is received.

The charging of the energy storage device is preferably already prevented within an end area of the first time period. This has the advantage that a possible effect on a relevant EMG sensor signal, e.g., due to a residual charging current, is prevented. The quality of the processed signal derived from the relevant EMG sensor signal is further improved hereby.

The measured signal amplifier is especially preferably coupled galvanically with a power supply unit during the first time period and is galvanically decoupled from the power supply unit during the second time period. A galvanic decoupling has the advantage that an adverse effect of a power supply unit galvanically coupled with the measured signal amplifier on a relevant EMG sensor signal is thus prevented.

The present invention will be explained in more detail below based on exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
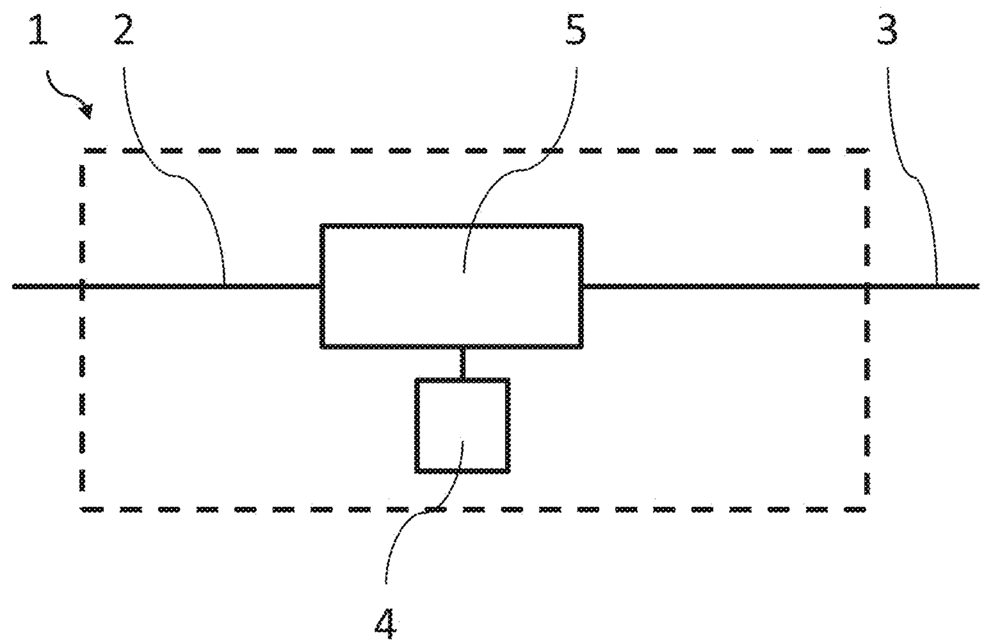
FIG. 1 is a schematic view showing a configuration of an embodiment of the measured signal amplifier according to the present invention.

Referring to the drawings, an embodiment of the measured signal amplifier according to the present invention 1 shown within a broken line in FIG. 1 has a central computer 5, a sensor interface 2, a device interface 3 as well as an energy storage device 4. An EMG sensor signal E (FIG. 2) can be introduced into the measured signal amplifier 1 via the sensor interface 2 and can be sent through to the computer 5. The computer 5 is configured to generate a processed signal V (not shown) from the EMG sensor signal E and to forward the processed signal via the device interface 3, e.g., to a therapy device and/or a display device. The device interface 3 is further configured to receive an energy signal for charging the energy storage device 4. The energy storage device 4 is configured, for example, as a capacitor and makes electrical current available to the computer 5. The computer 5 is further configured to control the charging of the energy storage device 4 as a function of the received EMG sensor signal E. The computer 5 is configured such as to make possible the charging of the energy storage device within a first time period T1 (see FIG. 2) and to prevent it within a second time period T2 (cf. FIG. 2).

Figure 2:
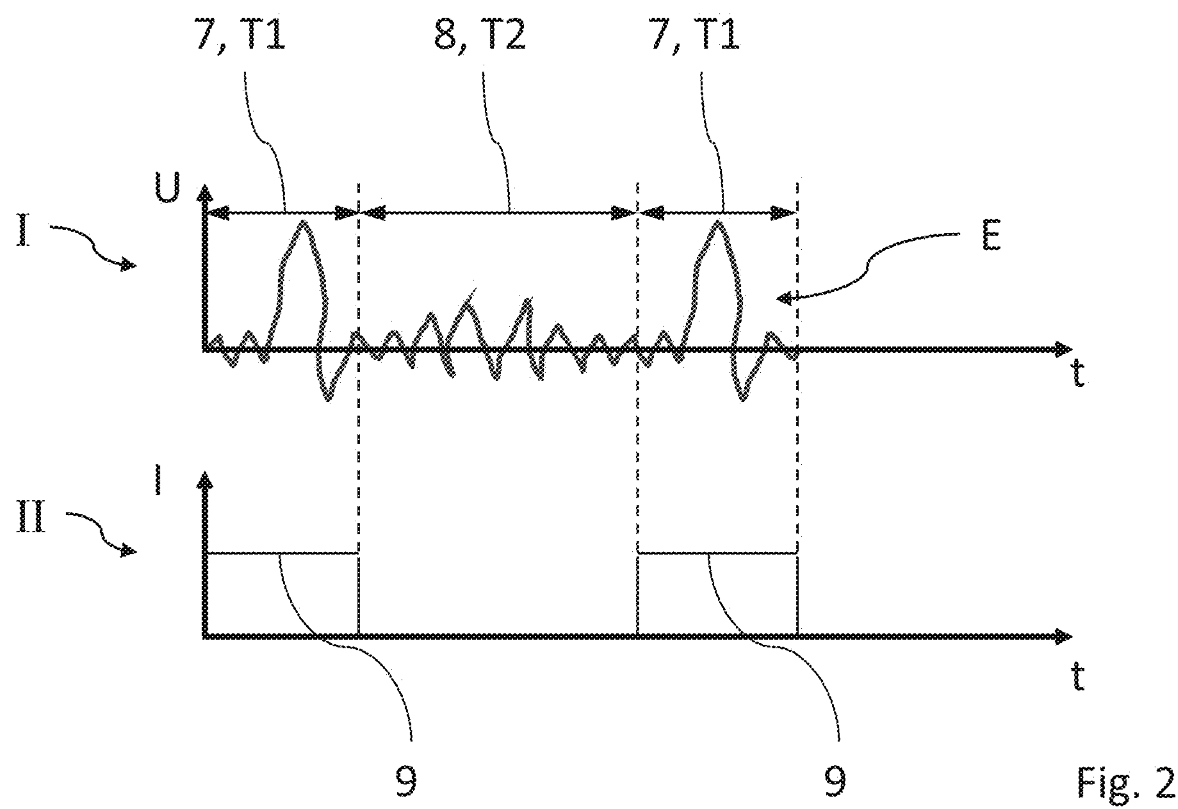
FIG. 2 is an EMG/ECG diagram in relation to charge cycles of the energy storage device.

A first diagram I in FIG. 2 shows electromyography signals (EMG signals), which are interfered with by electrocardiogram artifacts (ECG artifacts—all or a portion of the QRS complex). The diagram shows two first time periods T1, which are called ECG areas 7 and in which EMG signals are superimposed by relatively strong ECG artifacts, and a second time period T2, which is located between them, is called EMG area 8 and has only an EMG signal and no ECG artifacts. The signals measured in the ECG areas 7 cannot be used for the determination of an EMG signal and are therefore usually hidden. The ECG areas accordingly have irrelevant EMG sensor signals E and the EMG areas 8 have relevant EMG sensor signals E.

As is seen in diagram II, the first time periods T1 of the ECG areas 7 have a charging current with a charging current intensity 9, so that the energy storage device 4 is charged during these first time periods T1. The energy storage device 4 is decoupled from an external power supply unit during the time period T2 of the EMG area 8, so that the EMG area 8 has no charging current.

Figure 3:
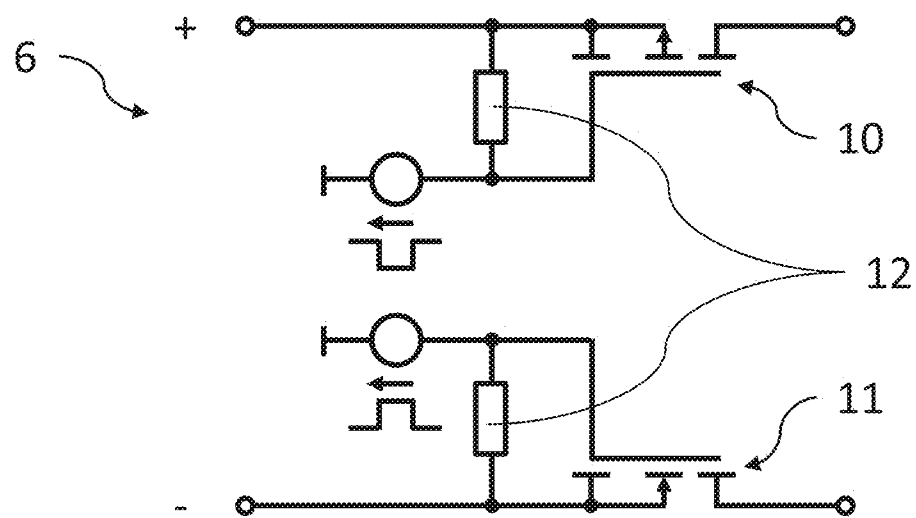
FIG. 3 is a schematic view showing first circuitry for reducing parasitic capacitances.

FIG. 3 schematically shows a first circuitry for reducing parasitic capacitances. The first circuitry is especially suitable for switching the power supply of the energy storage device 4. The first circuitry has a P-channel FET 10 ("Field Effect Transistor") in a positive branch and an N-channel FET 11 with a resistor 12 in a positive branch. If a control voltage corresponds to a supply voltage, the P-channel FET 10 decouples a line to be switched, e.g., the power supply line between the energy storage device 4 and an energy source. The N-channel FET 11 functions correspondingly. The P-channel FET 10 of this first circuitry may also be used to switch signal lines, e.g., the device interface 3 for outputting the processed signal V. To further minimize parasitic capacitances, the P-channel FET 10 and the N-channel FET 11 preferably have a low coupling capacity from the drain to the source.

Figure 4:
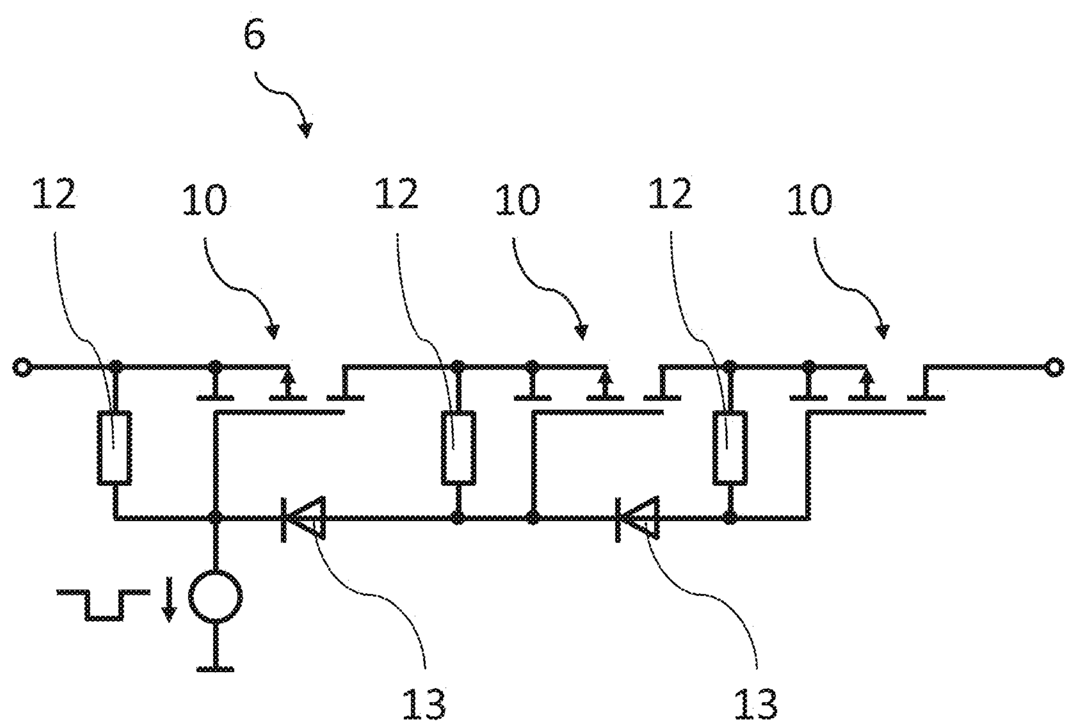
FIG. 4 is a schematic view showing second circuitry for reducing parasitic capacitances.

FIG. 4 schematically shows a second circuitry for reducing parasitic capacitances. The second circuitry is especially suitable for switching signal lines, e.g., the device interface 3, for outputting the processed signal V. Three P-channel FETs 10 are connected in series in this embodiment and are coupled with one another via an array of resistors 12 and diodes 13. A resulting capacitance is reduced due to the series connection of the P-channel FETs 10. Such a circuit with N-channel FETs 11 likewise leads to a reduction of a resulting capacitance and is therefore especially suitable for switching a negative supply voltage.

It is achieved due to the resistors 12 that a voltage between the gate and the source equals zero if a control voltage is not present, and that the P-channel FETs 10 as well as the N-channel FETs 11 interrupt a line. Here, the diodes 13 decouple the gate from the control voltage. By reducing the control voltage, the gates are brought to a low potential via the diodes 13 and thus they are conductive. The diodes 13 preferably have the lowest possible capacitance here. The P-channel FETs 10 as well as N-channel FETs 11 of the first circuitry and of the second circuitry are preferably configured as MOSFETs ("Metal Oxide Semiconductor Field Effect Transistors").

While specific embodiments of the invention have been shown and described in detail to illustrate the application of the principles of the invention, it will be understood that the invention may be embodied otherwise without departing from such principles.

The invention claimed is:

1. A measured signal amplifier for amplifying an EMG sensor signal, the measured signal amplifier comprising:

a sensor interface for receiving the EMG sensor signal;

at least one device interface for receiving an electrical energy signal as well as for transmitting a processed signal;

an electrically chargeable energy storage device; and at least one computer, wherein the computer is configured to:

derive the processed signal from the EMG sensor signal; and control the charging of the energy storage device with the electrical energy signal as a function of the EMG sensor signal received from the sensor interface including:

determining, on the basis of the received EMG sensor signal, a first time period, in which the EMG sensor signal has a heart signal component of a QRS complex and to control the charging the energy storage device such that the energy storage device is charged during the first time period; and determining, on the basis of the received EMG sensor signal, a second time period, in which the EMG sensor signal does not have a heart signal component of a QRS complex and to control the charging of the energy storage device such that charging of the energy storage device is prevented during the second time period.

2. A measured signal amplifier in accordance with claim 1, wherein the computer is further configured to prevent an output of the processed signal during the charging of the energy storage device.

3. A measured signal amplifier in accordance with claim 1, wherein the energy storage device has a capacitor.

4. A measured signal amplifier in accordance with claim 3, wherein the capacitor is a Gold Cap capacitor.

5. A medical system comprising:

at least one therapy device; and at least one EMG sensor for generating an EMG sensor signal, wherein the medical system has a measured signal amplifier comprising:

a sensor interface for receiving the EMG sensor signal;

at least one device interface for receiving an electrical energy signal as well as for transmitting a processed signal;

an electrically chargeable energy storage device; and at least one computer, wherein the computer is configured to:

derive the processed signal from the EMG sensor signal; and control the charging of the energy storage device with the electrical energy signal as a function of the EMG sensor signal received from the sensor interface including:

determining, on the basis of the received EMG sensor signal, a first time period, in which the EMG sensor signal has a heart signal component of a QRS complex and to control the charging of the energy storage device such that the energy storage device is charged during the first time period; and determining, on the basis of the received EMG sensor signal, a second time period, in which the EMG sensor signal does not have a heart signal component of a QRS and to control the charging of the energy storage device such that charging of the energy storage device is prevented during the second time period.

6. A medical system in accordance with claim 5, further comprising a power supply unit, which is configured for the intermittent supply of the energy storage device of the measured signal amplifier with electrical energy.

7. A measured signal amplifier in accordance with claim 2, wherein the energy storage device has a capacitor.

8. A measured signal amplifier in accordance with claim 7, wherein the capacitor is a Gold Cap capacitor.

9. A medical system in accordance with claim 5, wherein the computer is further configured to prevent an output of the processed signal during the charging of the energy storage device.

10. A medical system in accordance with claim 5, wherein the energy storage device has a capacitor.

11. A medical system in accordance with claim 10, wherein the capacitor is a Gold Cap capacitor.

12. A medical system in accordance with claim 9, wherein the energy storage device has a capacitor.

13. A medical system in accordance with claim 12, wherein the capacitor is a Gold Cap capacitor.

14. A measured signal amplifier, comprising:

a sensor interface configured for receiving an EMG sensor signal;

a device interface configured for receiving an electrical energy signal and for transmitting a processed signal;

an electrically chargeable energy storage device; and a computer configured to:

derive the processed signal from the EMG sensor signal; and control charging of the electrically chargeable energy storage device with the electrical energy signal based on the EMG sensor signal received from the sensor interface including:

determining, a first time period based on the received EMG sensor signal and to control the charging the energy storage device such that the energy storage device is charged during the first time period, the EMG sensor signal having a heart signal component of a QRS complex in the first time period; and determining, a second time period based on the received EMG sensor signal and to control the charging of the energy storage device such that charging of the energy storage device is prevented during the second time period, the EMG sensor signal being free of a heart signal component of a QRS complex in the second time period.

15. A measured signal amplifier in accordance with claim 14, wherein the computer is further configured to prevent an output of the processed signal during the charging of the energy storage device.

16. A measured signal amplifier in accordance with claim 14, wherein the energy storage device has a capacitor.

17. A measured signal amplifier in accordance with claim 16, wherein the capacitor is a Gold Cap capacitor.

* * * * *